Figure 1:
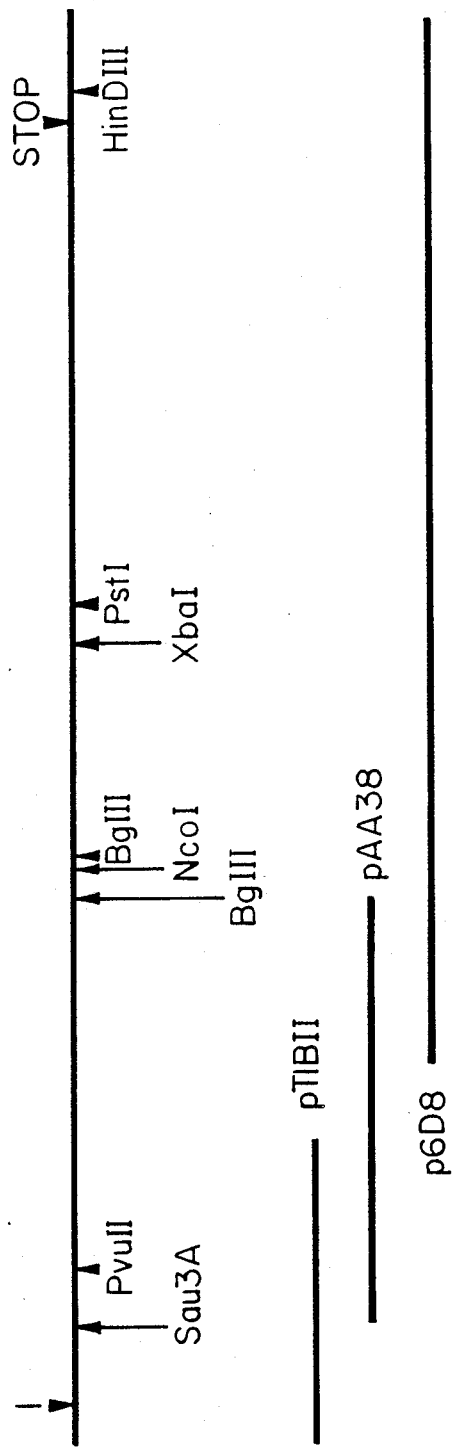
Figure 2A:
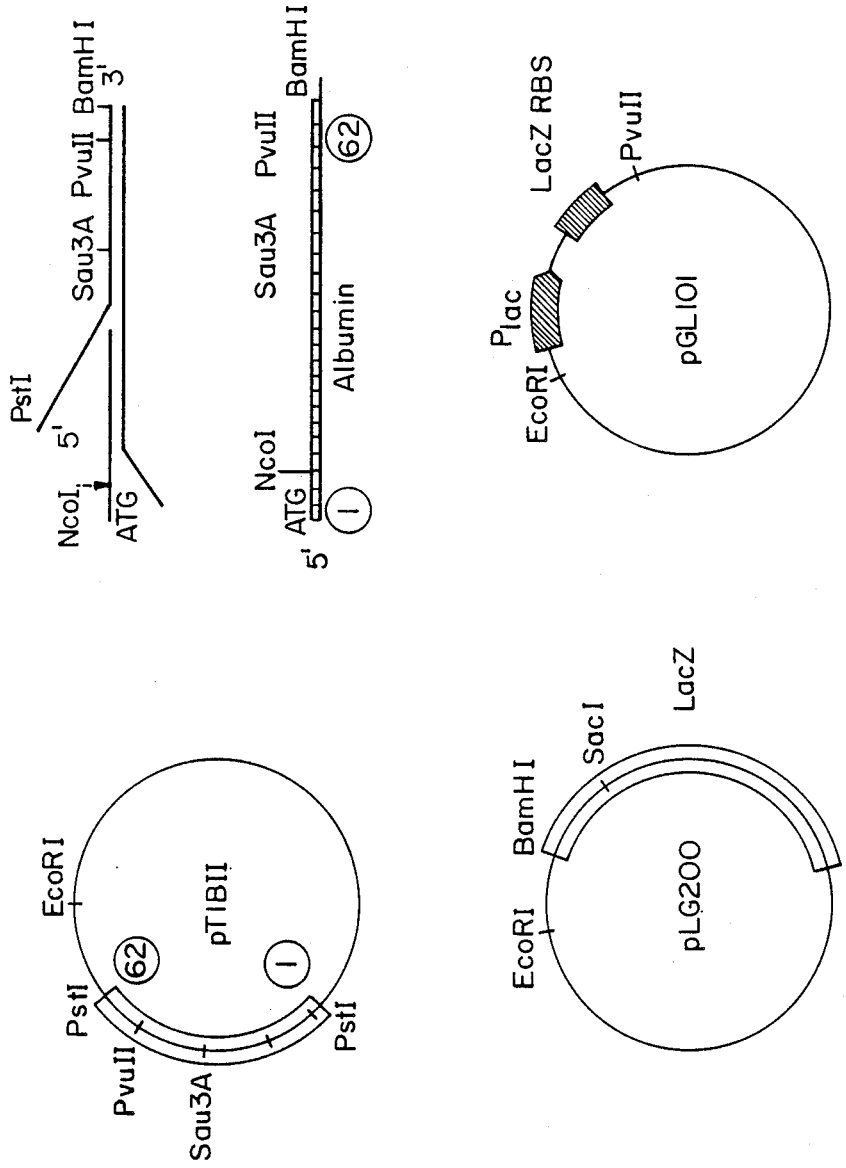
Figure 2B:
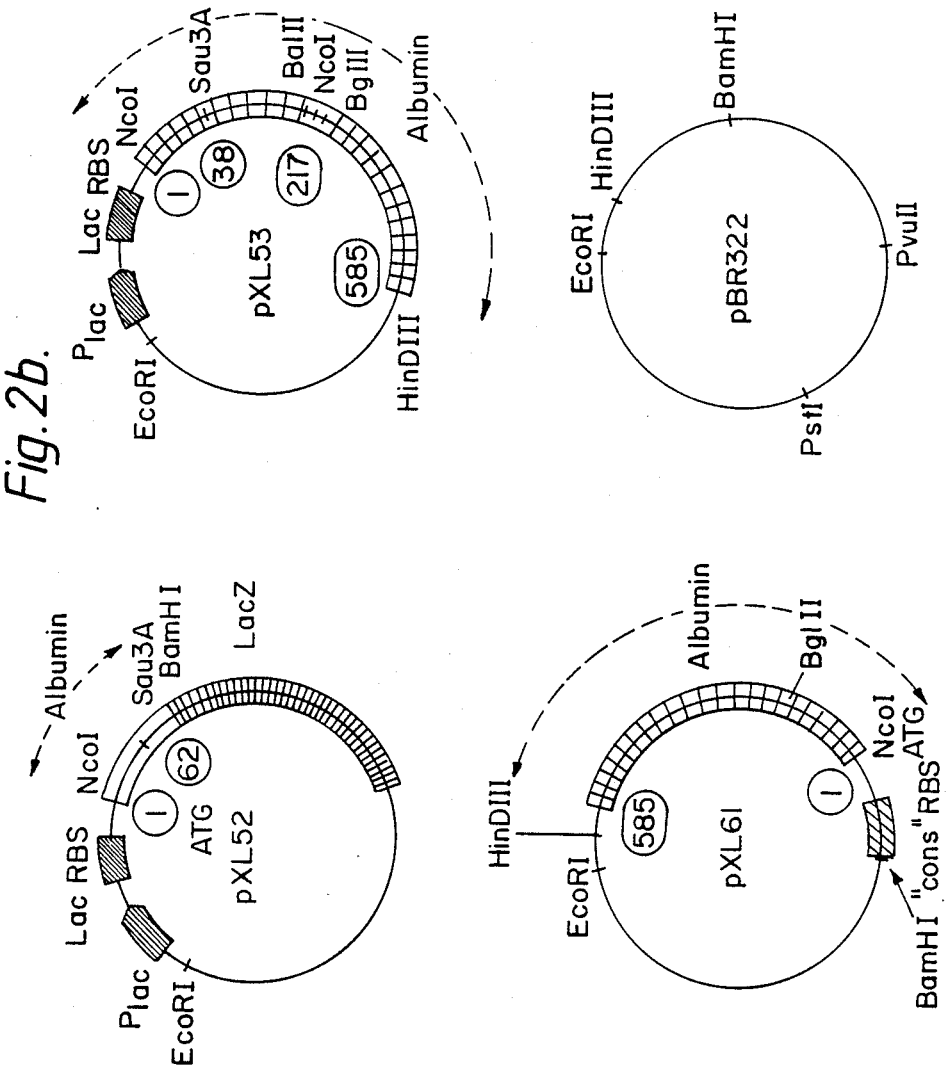
Figure 2C:
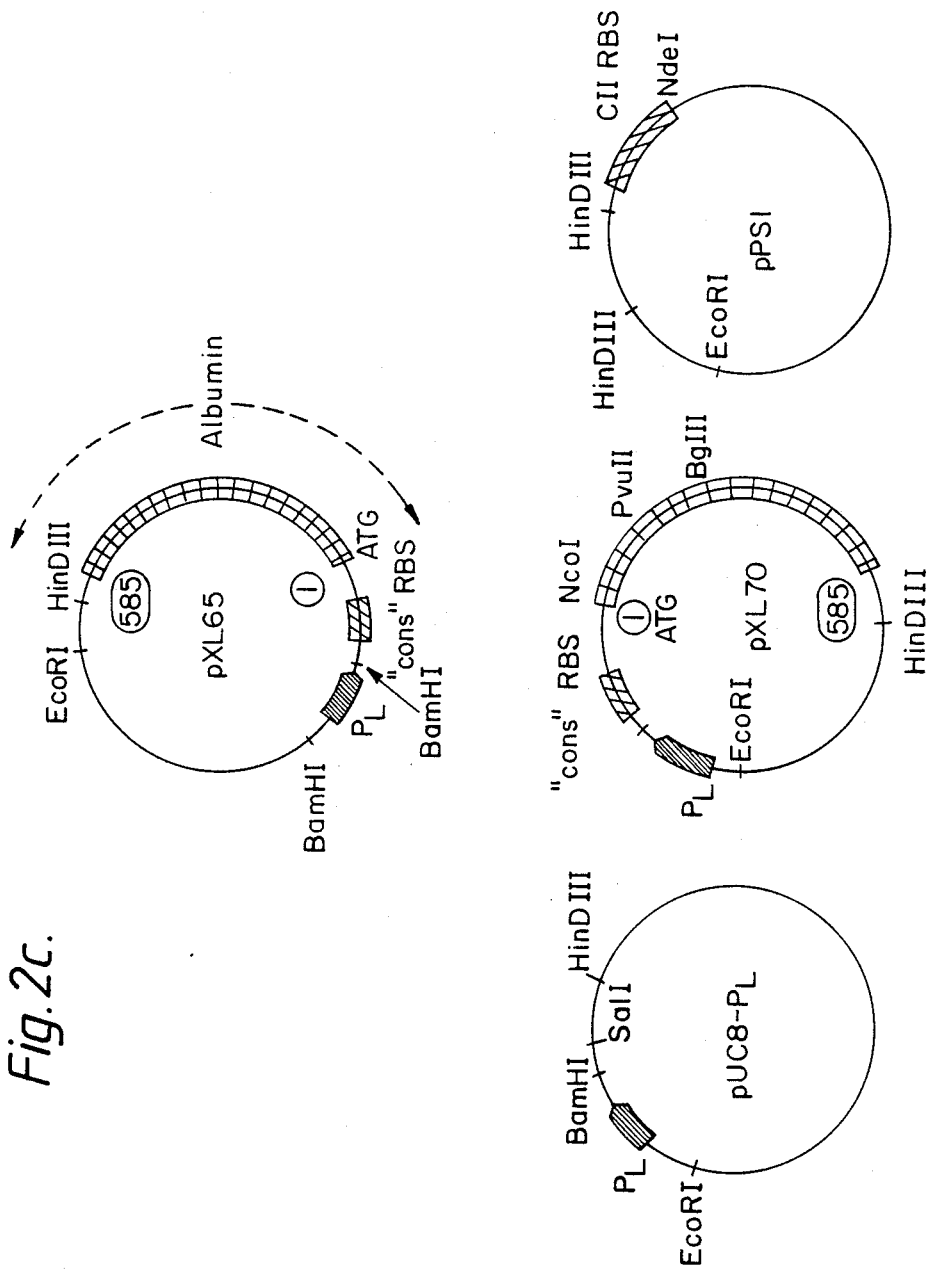
Figure 2D:
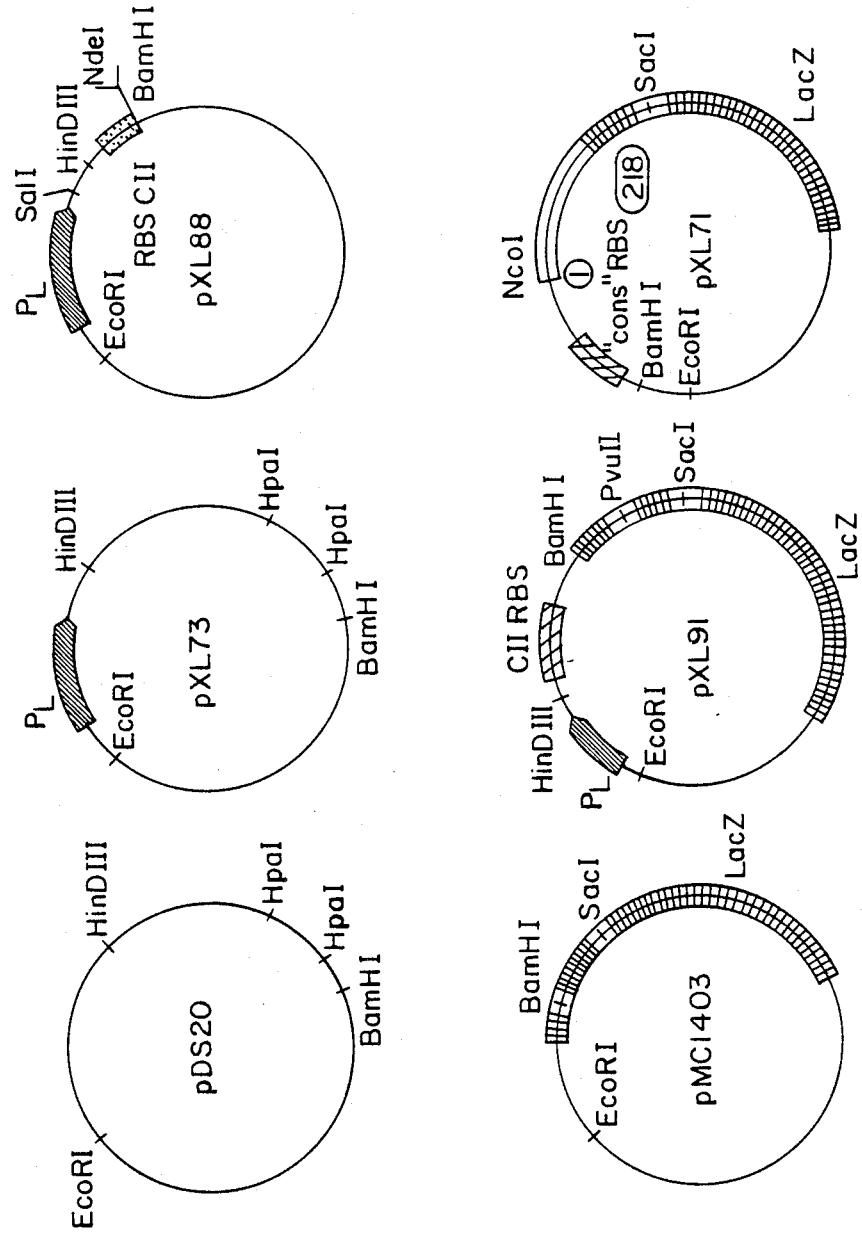
Figure 2E:
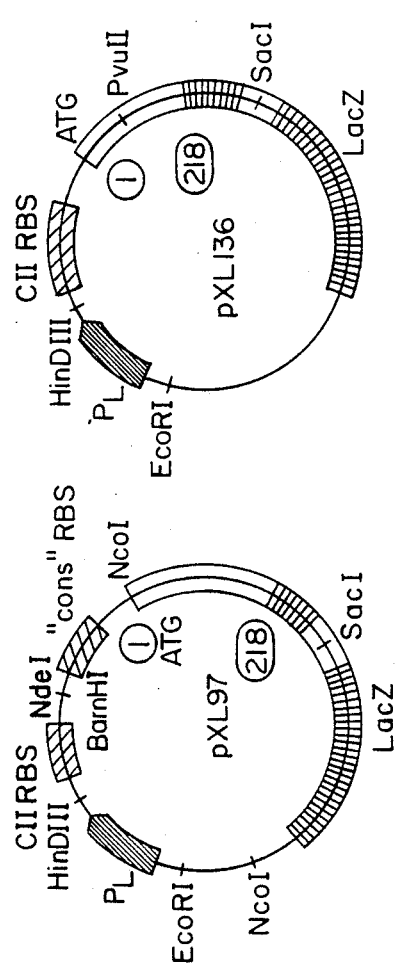
Figure 2E:
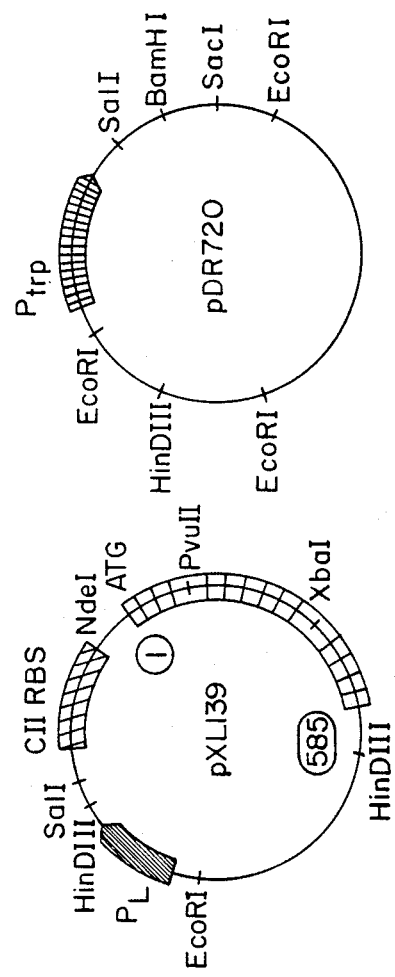
Figure 2F:
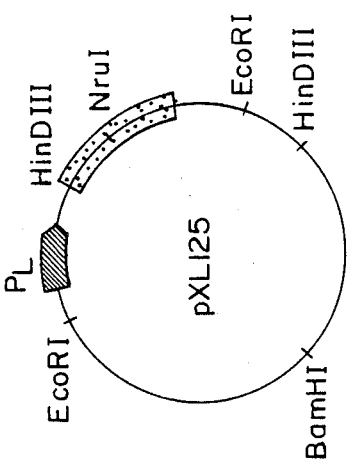
Figure 2F:
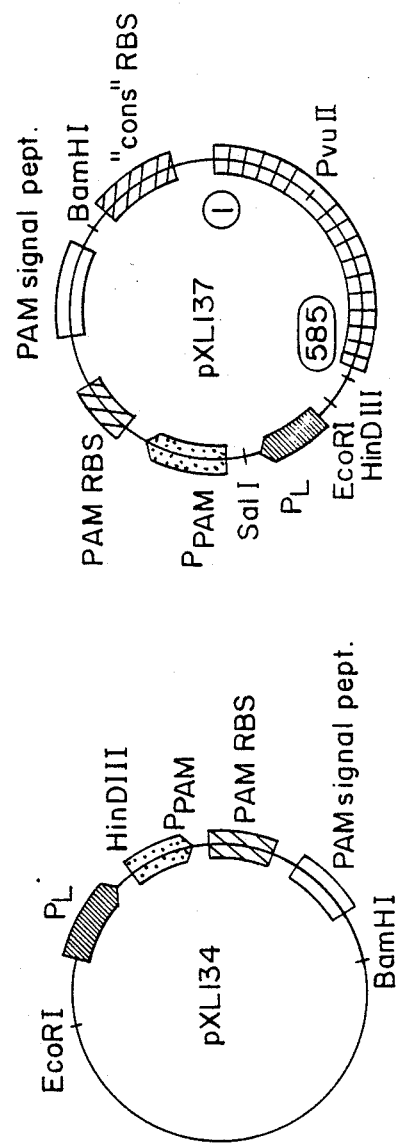
Figure 2F:
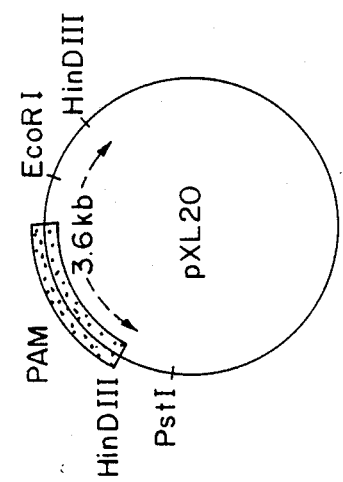
Figure 2G:
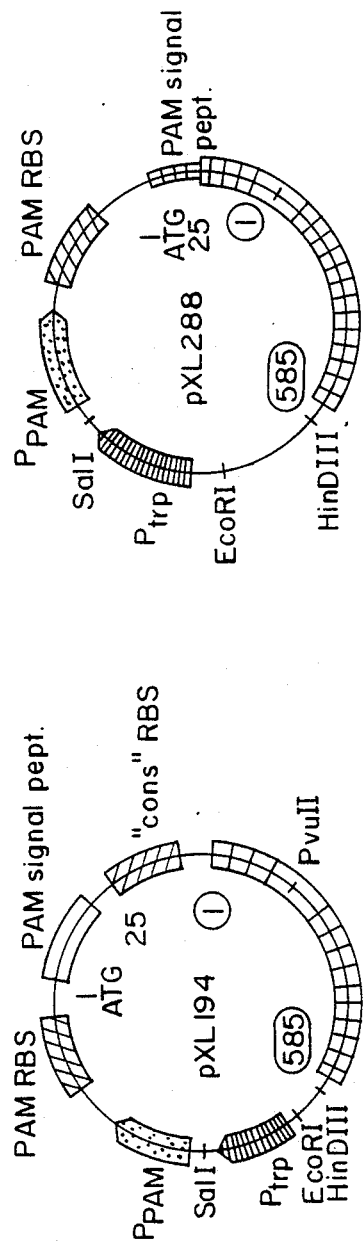

United States Patent [19]

Knapp et al.

[11] Patent Number: 4,914,027
[45] Date of Patent: Apr. 3, 1990

[54] PROCESS FOR THE MICROBIOLOGICAL PREPARATION OF HUMAN SERUM ALBUMIN

[75] Inventors: Michael Knapp; Georges Bréfort; Martine Latta, all of Paris; Jean-Francois Mayaux, Fontenay-aux-Roses; Paolo Sarmientos, Paris, all of France

[73] Assignee: Genetica, Joinville Le Pont, France

[21] Appl. No.: 843,725

[22] Filed: Mar. 25, 1986

[30] Foreign Application Priority Data

Mar. 25, 1985 [FR] France .................. 85 04385

[51] Int. Cl.⁴ .............. C12N 1/00; C12N 15/00; C12P 21/00; C12P 21/02
[52] U.S. Cl. .................. 435/69.6; 435/69.8; 435/172.3; 435/252.3; 435/252.33; 435/320; 530/350
[58] Field of Search ............ 435/68, 70, 172.3, 320; 935/41, 43, 44

[56] References Cited

U.S. PATENT DOCUMENTS 4,382,028  5/1983  Paget .................. 435/849
4,551,433  11/1985  Deboer ................ 435/253
4,666,836  5/1987  Inouye et al. ......... 435/68

FOREIGN PATENT DOCUMENTS 0107823  5/1984  European Pat. Off.

OTHER PUBLICATIONS

Nishi et al, Agric. Biol. Chem., vol. 48, pp. 669–675 (1984).
Lawn et al, Nucleic Acids Research, vol. 9, pp. 6103–6114 (1981).

Primary Examiner—Charles F. Warren
Assistant Examiner—Christopher S. F. Low
Attorney, Agent, or Firm—Stevens, Davis, Miller & Mosher

[57] ABSTRACT

Human serum albumin is produced by culturing a bacterium (e.g. *E. coli*) capable of maintaining a plasmid containing an inducible promoter (e.g. $P_{trp}$) upstream of the penicillin amidase promoter, the ribosome binding site of the penicillin amidase gene and the penicillin amidase signal peptide, fused with the structural gene for human serum albumin.

4 Claims, 23 Drawing Sheets

Restriction map of the human albumin gene and position of the insertions

The numeral 1 corresponds to the 1st amino acid of human albumin. The insertion of plasmid "pTIBII" extends beyond the 5' end, towards the proalbumin sequence.

Fig.3a.

pXL53 insertion sequence

```
EcoRI   10         20         30         40         50         60         70         80
GAATTCCTCACTCATTAGGCACCCCCAGGCCTTTACACATTTATGCTTCCGGGCTCGTATCGTTGTGTGGAATTGTGAGCGG 90         100        110        120        130        140        150        160
CTTAAGGAGTGAGTAATCCGTGGGGGTCGGAAAATGTAAATACGAAGCCGAGCATACAACACACCTTAACACTCGCC
ATAACAATTCACACAGGAAACAGGAATCCATGGATGCCACACAAGAGTGCTCATCGGTTTAAAGATTTGGGAGA 170        180        190        200        210        220        230        240
TATTGTTAAAGTGTGTCTCCTTTGTCCTTAGGTACCTACCTGTGTTCTCACTCCAACGAGTAGCCAAATTTCTAAACCCTCT
AGAAAATTTCAAAGCCTTGGTGTTGATTGCCTTTGCTCAGTATCTTCAGCAGTGTCCATTTGAAGATCATGTAAAATTAG 250        260        270        280        290        300        310        320
TCTTTTAAAGTTTCGGAACCACAACTAAGGAGTCATAGAAGTCGTCACAGGTAAACTTCTAGTACATTTTAATC
TGAATGAAGTAACTGAATTTGCAAAAACATGTGTTGCTGATGAGTCAGCTGAAAATTGTGACAAATCACTTCATACCCTT
ACTTACTTCATTGACTTAAAACGTTTTGTACACAACGACTACTCAGTCGGACTTTTAACACTGTTTAGTGAAGTATGGGAA
```

Fig. 3b.

```
         330       340       350       360       370       380       390       400
TTTGGAGACAAATTATGCACAGTTGCAACTCTTCGTGAAACCTATGGTGAAATGGCTGACTGCTGTGCAAAACAAGAACC 410       420       430       440       450       460       470       480
AAACCTCTGTTTAATACGGTGTCAACCTTGAGAAGCACTTTGGATACCACTTTACCGACTGACGACACGTTTGTTCTTGG

TGAGAGAAATGAATGCTTCTTGCAACACAAAGATGACAATCCAAATCTCCCCGATTGGTGAGACCAGAGAGGTTGATGTGA 490       500       510       520       530       540       550       560
ACTCTCTTTACTTACGGAGAACGTTGTGTTTCTACTGTTAGGTTTAGAGGGGCTAACCACTCTGGTCTCCAACTACACT

TGTGCAACTGCTTTTCATGACAATGAAGAGACATTTTGAAAAAATACTTATATGAAATTGCCAGAAGACATCCTTACTTT 570       580       590       600       610       620       630       640
ACACGGTGACGAAAAGTACTGTTACTTCTCTGTAAAAACTTTTTATGAATATACTTTAACGGTCTCTTCTGTAGGAATGAAA

TATGCCCCGGAACTCCTTTTCTTTGCTAAAAGGTATAAAGCTGCTTTTACAGAATGTTGCCAAGCTGCTGATAAAGCAGC

ATACGGGGCCTTGAGGAGAAAAGAAACGATTTTCCATATTTCGACGAAAATGTCTTACAACGGTTCGACGACTATTTCGTCG
```

Fig. 3c.

```
         650       660       670       680       690       700       710       720
CTGCCTGTTGCCAAAGCTCGATGAACTTCGGGATGAACTTCCTGCCAAGGGAAGGCTTCCTCTGCCAAACAGAGACTCAAGTGTGCCAGTC 730       740       750       760       770       780       790       800
GACGGACAACGGTTTCGAGCTACTTGAAGCCCTACTTCCCTTCCGAAGCAGAAGACGGTTTGTCTCTGAGTTCACACGGGTCAG

TCCAAAAATTTGGAGAAAGAGCTTTCGAAAGCATGGGCAGTAGCTCGCCTGAGCCAGAGATTTCCCAAAGCTGAGTTTGCA

AGGTTTTTAAACCTCTCTTTCTCGAAAGTTTCGTACCCGTCATCGAGCGGACTCGGTCTCTAAAGGGTTTCGACTCAAACGT 810       820       830       840       850       860       870       880
GAAGTTTCCAAGTTAGTGACAGATCTTACCAAAGTCCAGATGCTGCCATGGAGATCTGCTTGAATGCTGATGA

CTTCAAAGGTTCAATCACTGTCTAGAATGGTTTCAGGTGTGCCTTACGACGGTACCCTCTAGACGAACTTACACGACTACT 890       900       910       920       930       940       950       960
CAGGGGCGGACCTTGCCAAGTATATCTGTGAAAATCAAGATTCGATCTCCAGTAAACTGAAGGAATGCTGTGAAAAACCTC

GTCCCGCCTGGAACGGTTCATATAGACACTTTTAGTTCTAAGCTAGAGGTCATTTGACTTCCTTACGACACTTTTGGAG
```

Fig.3d.

```
       970       980       990      1000      1010      1020      1030      1040
TGTTGGAAAAATCCCACTGCATTGCCGAAGTGGAAAATGATGAGATGCCTGCTGACTTGCCTTCATTAGCGGCTGATTTT 1050      1060      1070      1080      1090      1100      1110      1120
ACAACCTTTTTAGGGTGACGTAACGGCTTCACCTTTTACTACTCTACGGACGACTGAACGGAAGTAATCGCCGACTAAAA 1130      1140      1150      1160      1170      1180      1190      1200
GTTGAAAGTAAGGATGTTTGCAAAAACTATGCTGAGGCAAAGGATGTCTTCTTGGGCATGTTTTGTATGAATATGCAAG

CAACTTTCATTCCTACAAACGTTTTTGATACGACTCCGTTTCCTACAGAAGAACCCGTACAAAAACATACTTATACGTTC 1210      1220      1230      1240      1250      1260      1270      1280
AAGGCATCCTGATTACTCTGTCCTACTGCTGCTGAGACTTGCCAAGACATATGAAACCACTCTAGAGAAGTGCTGTGCCG

TTCCGTAGGACTAATGAGACAGCATGACGACGACTCTGAACGGTTCTGTATACTTTGGTGAGATCTCTTCACGACACGGC

CTGCAGATCCTCATGAATGCTATGCCAAAGTGTTCGATGAATTTAAACCTCTTATGGAAGAGCCCTCAGAATTTAATCAAA

GACCGTCTAGGAGTACTTACGATACGGTTTCACAAGCTACTTAAATTTGGAGAATACCTTCTCGGAGTCTTAAATTAGTTT
```

Fig. 3e.

```
     1290      1300      1310      1320      1330      1340      1350      1360
CAAAATTGTGAGCTTTTTGAGCAGCTTGGAGAGTACAAATTCCAGAATGCGCTATTAGTTCGTTACACCAAGAAAGTACC

GTTTTAACACTCGAAAAACTCGTCGAACCTCTCATGTTAAGGTCTTACGCGATAATCAAGCAATGTGGTTCTTTCATGG 1370      1380      1390      1400      1410      1420      1430      1440
CCAAGTGTCAAACTCCAACTCTTGTAGAGGTCTCAAGAAACCTAGGAAAAGTGGGCAGCAAATGTTGTAAACATCCTGAAG

GGTTCACAGAGTTGAGGTTGAGAACATCTCCAGAGTTCTTTGGATCCTTTCACCCGTCGTTTACAACATTTGTAGGACTTC 1450      1460      1470      1480      1490      1500      1510      1520
CAAAAAGAATGCCCTGTGCAGAAGACTATCTATCCGTGGTCCTGAACCTGGTCTGTTGCATGAGAAAACGCCAGTA

GTTTTCTTACGGGACACGTCTTCTGATAGATAGGCACCAGGACTTGGTCAATACACAACGTACTCTTTTGCGGTCAT 1530      1540      1550      1560      1570      1580      1590      1600
AGTGACAGAGTCACCAAATGCTGCACAGAATCCTTGGTGAACAGGGACCATGCTTTCAGCTCTCGGAAGTCGATGAAAC

TCACTGTCTCAGTGGTTTACGACGTGTCTTAGGAACCACTTGTCCGCTGGTACGAAAAGTCGAGACCTTCAGCTACTTTG
```

Fig. 3g.

```
         1930      1940      1950      1960      1970      1980      1990      2000
ATGAAGATCAAAAGCTTATTCATTCTGTTTTCTTTTCGTTGGTGTCTAAAAGCCAACACCCTCTCTAAAAAACATAAATT
TACTTCTAGTTTTCGAATAAGTAAGACAAAAGAAAAAGCCAACCACATTTTCGGTTGTGGGACAGATTTTTGTATTTAA 2010      2020      2030      2040      2050      2060      2070      2080
TCTTTAATCATTTAATCATTTGCCTCTTTTCTCTGTGCCTTCAATTAATAAAAATGGAAAGAATCTAAAAAAACCCCC
AGAAATTAGTAAAATTAGTAAAACGGAGAAAAGAGACGAAGTTAATTATTTTTACCTTTTCTTAGATTTTTTGGGGG 2090      2100      2110      2120      2130      2140      2150      2160
           PstI
CCCCCCCCCCCCAGCAATAGCAACAACGTTGCGCAAACTATTAACTGGGCGAA
GGGGGGGGGGGGACGTCGTTATCGTTGTTGCAACGCGTTTGATAATTGACCCGCTT
```

Fig. 4a.

Translation of the human albumin gene in pXL53

①
```
                125                 140                 155                 170
ATG GAT GCA CAC AAG AGT GAG GTT GCT CAT CGG TTT AAA GAT TTG GGA GAA GAA AAT TTC
MET ASP ALA HIS LYS SER GLU VAL ALA HIS ARG PHE LYS ASP LEU GLY GLU GLU ASN PHE 185                 200                 215                 230
AAA GCC TTG GTG TTG ATT GCC TTT GCT CAG TAT CTT CAG CAG TGT CCA TTT GAA GAT CAT
LYS ALA LEU VAL LEU ILE ALA PHE ALA GLN TYR LEU GLN GLN CYS PRO PHE GLU ASP HIS 245                 260                 275                 290
GTA AAA TTA GTG AAT GAA GTA ACT GAA TTT GCA AAA ACA TGT GTT GCT GAT GAG TCA GCT
VAL LYS LEU VAL ASN GLU VAL THR GLU PHE ALA LYS THR CYS VAL ALA ASP GLU SER ALA 305                 320                 335                 350
GAA AAT TGT GAC AAA TCA CTT CAT ACC CTT TTT GGA GAC AAA TTA TGC ACA GTT GCA ACT
GLU ASN CYS ASP LYS SER LEU HIS THR LEU PHE GLY ASP LYS LEU CYS THR VAL ALA THR
```

Fig. 4b.

```
                    365                    380                    395                    410
CTT  CGT  GAA  ACC  TAT  GGT  GAA  ATG  GCT  GAC  TGC  TGT  GCA  AAA  CAA  GAA  CCT  GAG  AGA  AAT
LEU  ARG  GLU  THR  TYR  GLY  GLU  MET  ALA  ASP  CYS  CYS  ALA  LYS  GLN  GLU  PRO  GLU  ARG  ASN 425                    440                    455                    470
GAA  TGC  TTC  TTC  CAA  CAC  AAA  GAT  GAC  AAT  CCA  AAT  CTC  CCC  CGA  TTG  GTG  AGA  CCA  GAG
GLU  CYS  PHE  PHE  LEU  GLN  HIS  LYS  ASP  ASP  ASN  PRO  ASN  LEU  PRO  ARG  LEU  VAL  ARG  PRO  GLU 485                    500                    515                    530
GTT  GAT  GTG  ATG  TGC  ACT  GCT  TTT  CAT  GAC  AAT  GAA  GAG  ACA  TTT  AAA  AAA  TAC  TTA
VAL  ASP  VAL  MET  CYS  THR  ALA  PHE  HIS  ASP  ASN  GLU  GLU  THR  PHE  LYS  LYS  TYR  LEU 545                    560                    575                    590
TAT  GAA  ATT  GCC  AGA  AGA  CAT  CCT  TAC  TTT  TAT  GCC  CCG  GAA  CTC  CTT  TTC  TTT  GCT  AAA
TYR  GLU  ILE  ALA  ARG  ARG  HIS  PRO  TYR  PHE  TYR  ALA  PRO  GLU  LEU  LEU  PHE  PHE  ALA  LYS
```

Fig.4c.

```
                                                                    605                      620                      635                      650
AGG  TAT  AAA  GCT  TTT  ACA  GAA  TGT  TGC  CAA  GCT  GCT  GAT  AAA  GCA  GCC  TGC  CTG  TTG
ARG  TYR  LYS  ALA  PHE  THR  GLU  CYS  CYS  GLN  ALA  ALA  ASP  LYS  ALA  ALA  CYS  LEU  LEU 665                      680                      695                      710
CCA  AAG  CTC  GAT  GAA  CTT  CGG  GAT  GAA  GGG  AAG  GCT  TCG  TCT  GCC  AAA  CAG  AGA  CTC  AAG
PRO  LYS  LEU  ASP  GLU  LEU  ARG  ASP  GLU  GLY  LYS  ALA  SER  SER  ALA  LYS  GLN  ARG  LEU  LYS 725                      740                      755                      770
TGT  GCC  AGT  CTC  CAA  AAA  TTT  GGA  GAA  AGA  GCT  TTC  AAA  GCA  TGG  GCA  GTA  GCT  CGC  CTC
CYS  ALA  SER  LEU  GLN  LYS  PHE  GLY  GLU  ARG  ALA  PHE  LYS  ALA  TRP  ALA  VAL  ALA  ARG  LEU 785                      800                      815                      830
AGC  CAG  AGA  TTT  CCC  AAA  GCT  GAG  TTT  GCA  GAA  GTT  TCC  AAG  TTA  GTG  ACA  GAT  CTT  ACC
SER  GLN  ARG  PHE  PRO  LYS  ALA  GLU  PHE  ALA  GLU  VAL  SER  LYS  LEU  VAL  THR  ASP  LEU  THR
```

Fig.4d.

```
      845              860              875              890
AAA GTC CAC ACG GAA TGC CAT GGA GAT CTC CTT GAA TGT GCT GAT GAC ACG GCG GAC
LYS VAL HIS THR GLU CYS HIS GLY ASP LEU LEU GLU CYS ALA ASP ASP ARG ALA ASP 905              920              935              950
CTT GCC AAG TAT ATC TGT GAA AAT CAA GAT TCC ATC TCC AGT AAA CTC AAG GAA TGC TGT
LEU ALA LYS TYR ILE CYS GLU ASN GLN ASP SER ILE SER SER LYS LEU LYS GLU CYS CYS 965              980              995             1010
GAA AAA CCT CTG TTG GAA AAA TCC CAC TGC ATT GCC GAA GTG GAA AAT GAT GAG ATG CCT
GLU LYS PRO LEU LEU GLU LYS SER HIS CYS ILE ALA GLU VAL GLU ASN ASP GLU MET PRO 1025             1040             1055             1070
GCT GAC TTG CCT TCA TTA GCG GCT GAT TTT GTT GAA AGT AAG GAT GTT TGC AAA AAC TAT
ALA ASP LEU PRO SER LEU ALA ALA ASP PHE VAL GLU SER LYS ASP VAL CYS LYS ASN TYR
```

Fig.4e.

```
                                           1085
GCT GAG GCA AAG GAT GTC TTC TTG  
ALA GLU ALA LYS ASP VAL PHE LEU 1100                    1115                    1130
GGC ATG TTT TAT GAA TGC AGA AGG CAT CCT
GLY MET PHE TYR GLU TYR ALA ARG ARG HIS PRO

1145
GAT TAC TCT GTC GTA CTG CTG CTG AGA CTT GCC AAG ACA TAT GAA ACC ACT CTA GAG AAG
ASP TYR SER VAL VAL LEU LEU LEU ARG LEU ALA LYS THR TYR GLU THR THR LEU GLU LYS
         1160                    1175                    1190

1205
TGC TGT GCC GCT GCA GAT CCT CAT GAA TGC TAT GCC AAA GTG TTC GAT GAA TTT AAA CCT
CYS CYS ALA ALA ALA ASP PRO HIS GLU CYS TYR ALA LYS VAL PHE ASP GLU PHE LYS PRO
         1220                    1235                    1250

1265
CTT ATG GAA GAG CCT CAG AAT TTA ATC AAA CAA AAT TGT GAG CTT TTT GAG CAG CTT GGA
LEU MET GLU GLU PRO GLN ASN LEU ILE LYS GLN ASN CYS GLU LEU PHE GLU GLN LEU GLY
         1280                    1295                    1310
```

Fig.4f.

```
                         1325                 1340                 1355                 1370
GAG TAC AAA TTC CAG AAT GCG CTA TTA GTT CGT TAC ACC AAG AAA GTA CCC CAA GTG TCA
GLU TYR LYS PHE GLN ASN ALA LEU LEU VAL ARG TYR THR LYS LYS VAL PRO GLN VAL SER 1385                 1400                 1415                 1430
ACT CCA ACT CTT GTA GAG GTC TCA AGA AAC CTA GGA AAA GTG GGC AGC AAA TGT TGT AAA
THR PRO THR LEU VAL GLU VAL SER ARG ASN LEU GLY LYS VAL GLY SER LYS CYS CYS LYS 1445                 1460                 1475                 1490
CAT CCT GAA GCA AAA AGA ATG CCC TGT GCA GAA GAC TAT CTA TCC GTG GTC CTG AAC CAG
HIS PRO GLU ALA LYS ARG MET PRO CYS ALA GLU ASP TYR LEU SER VAL VAL LEU ASN GLN 1505                 1520                 1535                 1550
TTA TGT GTG TTG CAT GAG AAA ACG CCA GTA AGT GAC AGA GTC ACC AAA TGC TGC ACA GAA
LEU CYS VAL LEU HIS GLU LYS THR PRO VAL SER ASP ARG VAL THR LYS CYS CYS THR GLU
```

Fig.4g.

```
            1565                    1580                    1595              1610
TCC TTG GTG AAC AGG CGA CCA TGC TTT TCA GCT CTG GAA GTC GAT GAA ACA TAC GTT CCC
SER LEU VAL ASN ARG ARG PRO CYS PHE SER ALA LEU GLU VAL ASP GLU THR TYR VAL PRO 1625                    1640                    1655              1670
AAA GAG TTT AAT GCT GAA ACA TTC ACC TTC CAT CCA GAT ATA TGC ACA CTT TCT GAG AAG
LYS GLU PHE ASN ALA GLU THR PHE THR PHE HIS ALA ASP ILE CYS THR LEU SER GLU LYS 1685                    1700                    1715              1730
GAG AGA CAA ATC AAG AAA CAA ACT GCA CTT GTT GAG CTT GTG AAA CAC AAG CCC AAG GCA
GLU ARG GLN ILE LYS LYS GLN THR ALA LEU VAL GLU LEU VAL LYS HIS LYS PRO LYS ALA 1745                    1760                    1775              1790
ACA AAA GAG CAA CTG AAA GCT GTT GCT GAT GAT TTC GCA GCT TTT GTA GAG AAG TGC TGC
THR LYS GLU GLN LEU LYS ALA VAL MET ASP ASP PHE ALA ALA PHE VAL GLU LYS CYS CYS
```

Fig. 4h.

```
                                      1805                    1820                    1835              1850
AAG GCT GAC GAT AAG GAA ACC TGC TTT GCC GAG GAG GCT AAA AAA CTT GCT GCA AGT
LYS ALA ASP ASP LYS GLU THR CYS PHE ALA GLU GLU GLY LYS LYS LEU VAL ALA SER 1865                 (585-STOP)    1880
CAA GCT GCC TTA GGC TTA TAA CAT CAC ATT
GLN ALA ALA LEU GLY LEU

THE MOLECULAR WEIGHT OF THIS PROTEIN IS 66550.0
```

PROCESS FOR THE MICROBIOLOGICAL PREPARATION OF HUMAN SERUM ALBUMIN

The present invention relates to protein synthesis.

More especially, the invention provides a process for the synthesis of human serum albumin by a bacterium, which has been subjected to in vitro genetic manipulation techniques to obtain a concerted rearrangement of deoxyribonucleic acid sequences.

Human serum albumin is a protein consisting of 585 amino acids which does not contain associated glycoside residues and has a molecular weight of the order of 66,000 daltons.

Genetically, human serum albumin is encoded in man by two codominant autosomal allelic genes. The genes for human serum albumin are notoriously polymorphic, and at least twenty-four variants of serum albumin are known, differentiated by their electrophoretic behaviour (Shell and Blumberg, "The genetics of human serum albumin", in "Albumin Structure, Function and Uses", Rosenoer, Oratz and Rothschild eds., Pergamon Press, 1977).

Serum albumin is synthesized in the hepatocytes, and then excreted into the serum in which it constitutes the most abundant protein, with mean concentrations of the order of 4 g/100 ml of serum. It performs a major physiological role in the maintenance of the oncotic pressure of the plasma, and thus contributes to the stability of the balance between the internal (cellular) environment and the external (circulating) environment, which balance provides, among other functions, for the maintenance of a level of cell hydration which is compatible with the normal physiological functioning of the body.

Human serum albumin also performs a role in the transport of "natural" hydrophobic molecules (steroids and bile salts, for example) and drug molecules to their sites of action.

This explains why human serum albumin is used both in the therapy of blood volume disorders, for example posthaemorrhagic acute hypovolaemia or extensive burns, and in supportive therapy in so-called volume expansion solutions in general surgery, and in the treatment of dehydration states (for example nephrotic syndromes), all these uses demanding the supply of considerable amounts of serum albumin (several tens of grammes per day per patient).

Human serum albumin is at present extracted from serum by techniques derived from that of E. J. Cohn et al., J. Am. Chem. Soc. (1946), 68, p. 459 et seq., or from placenta by the technique of J. Liautaud et al., 13th Internat. Congress of IABS, Budapest; A: Purification of Proteins. Development of Biological Standard (1973) Karger, ed., Bale, 27, p. 107 et seq. These sources, which hardly meet the requirements of the world market, suffer from several defects, inter alia their uncertain nature. Moreover, they are not devoid of the risk of contamination (hepatitis, for example, and more recently acquired immunodeficiency syndrome), and this would have dramatic consequences when the protein was used in therapy.

In vitro genetic recombination techniques now offer the possibility of making a micro-organism, for example the *Escherichia coli* bacterium, synthesize any protein or any polypeptide and, in theory, doing this in unlimited quantities (see for example F. Gros et al., Sciences de La Vie et Société, Documentation Francaise ed., 1979).

Since the classical experiments of F. Jacob et al., it is known that DNA contains, on the one hand a group of so-called "structural" genes, that is to say genes which code for a given protein, and on the other hand so-called "regulator" genes, that is to say genes capable of modulating the expression of the structural genes, the combination of the two types forming an entity known as an "operon".

Research in molecular biology and the development of DNA sequencing techniques [F. Sanger and A. R. Coulson, J. Mol. Biol. (1975), 94, p. 441 et seq., A. M. Maxam and W. Gilbert, Proc. Natl. Acad. Sci. (USA) (1977), 74, p. 560 et seq.] have made it possible to specify the organization of the operon as it had been conceived by F. Jacob and J. Monod [F. Jacob and J. Monod, Cold Spring Harbor Symp. Quant. Biol. (1961), 26, p. 193 et seq.; F. Jacob and J. Monod, J. Mol. Biol. (1961), 26 p. 318 et seq.], and to identify the special features of the primary structure of the two types of gene.

Thus, all structural genes are enclosed by a so-called "translation initiation" codon (ATG) and a "stop" codon. The function of the initiation codon is to bind a transfer RNA bearing a formylmethionine. The protein chain will elongate from this formylmethionine by successive attachment of amino acids encoded by the structural gene; the "stop" codon will finally cause the elongation to stop and bring about the release of the newly formed protein.

As regards the regulating genes (promoters, repressors), a promoter, for example, being defined as a DNA fragment to which RNA polymerase is bound, it has been possible to identify the most highly conserved sequences [D. Pribnow, Proc. Natl. Acad. Sci. (USA) (1975), 72, p. 784 et seq.]; similarly, it has been possible to define the most highly conserved DNA sequences at the level of the ribosome binding sites (RBS) [J. Shine and L. Dalgarno, Nature (1975), 254, p. 34 et seq.], which sites perform a role in the translation of the transcribed RNA to protein.

Thus, the bacterial regulator genes can hence be defined by their functional properties and also by their primary sequence, and in vitro genetic recombination techniques turn this to good account to place any structural gene under their control, this being possible as a result of the existence of "restriction enzymes" which cut the DNA at specific points [H. O. Smith and K. W. Wilcox, J. Mol. Biol. (1970), 51, p. 379 et seq., M. Meselson and R. Yuan, Nature (1968), 217, p. 1110 et seq., R. J. Roberts, Nucleic Acids Res. (1982), 1, p. 135 et seq.].

The techniques used, which are in other respects known, employ the concerted use of these enzymes to cut the DNA at predetermined points, and enzymes known as "ligases" to link the fragments together [P. E. Loban and A. D. Kaiser, J. Mol. Biol. (1973), 78, p. 453 et seq.] The assembly is carried by "vectors" (plasmids or bacteriophages) capable of being introduced into a bacterium such as *E. coli* by processes which are in other respects known, and of being maintained there during the growth of the host bacterium [M. Mandel and A. Higa, J. Mol. Biol. (1970), 53, p. 154 et seq.].

Thus, the present invention provides a process for the biosynthesis of human serum albumin in a microorganism.

To achieve this objective the structural gene for human serum albumin is modified in such a manner that it possesses an initiation codon, and the modified structural gene is then linked to an inducible regulator gene.

Culture of a host bacterium, such as *E. coli*, containing the modified gene produces a useful amount of albumin after induction under defined conditions.

In that which follows, the technical terms of molecular biology are used in their normal sense [see, for example, "Molecular Biology of the Gene" by J. Watson (French edition, Interéditions 1978)]. In that which follows, the construction and the processes used for expression of the human serum albumin gene are described successively.

A. CONSTRUCTION OF THE HUMAN SERUM ALBUMIN GENE

1. Preparation of Liver messenger RNA

Liver cells are used, obtained, for example, by biopsy, and the messenger RNA is extracted therefrom according to the method described, for example, by V. Glisin et al., Biochemistry (1974), 13, p. 2633 et seq.; and by R. Deeley et al., J. Biol. Chem. (1977), 252, p. 8310 et seq. The biopsy is treated with 6M guanidine thiocyanate solution and the total RNA is purified by several cycles of precipitation in ethanol at −20° C., centrifugation and redissolution of the centrifugation pellets.

The preparation is enriched in messenger RNA by several cycles of affinity chromatography on columns of oligo(dT)-cellulose according to the technique described by H. Aviv and P. Leder, Proc. Natl. Acad. Sci. (USA) (1972), 69, p. 1408 et seq. The messenger RNA thus isolated, containing 1 to 2% of total RNA, is stored in aqueous solution at −70° C.

It is possible to determine the proportion of messenger RNA specific for human serum albumin within the total population (for example by in vitro translation of an aliquot of the RNA solution in rabbit reticulocyte lysates). One method consists in using the reticulocyte lysate supplied by Amersham, following the procedure recommended by this supplier. Thus, it is possible to determine the fraction of newly formed protein which is immunoprecipitable by anti-albumin antibodies within the whole group of newly formed proteins. A fraction, for example, of the order of 6% is obtained.

2. Synthesis of cDNA and cloning in *E. coli*.

a. Synthesis of the first strand

Starting with a modification of the technique of G. N. Buell et al., J. Biol. Chem. (1978), 253, p. 2471 et seq., 5 μg of total messenger RNA, for example, are used in a final volume of 50 microliters of a solution containing: 100 mM Tris.HCl pH 8.3, 10 mM $MgCl_2$, 0.4 mM DTT, 20 mM KCl, 0.4 mM Na pyrophosphate, 1 mM with respect to each nucleotide triphosphate (dNTP), 100 μg/ml of oligo(dt)$_{12-18}$, 0.5 U/ml of ribonuclease inhibitor, 50 picomoles of radioactive tracer and 40 units of reverse transcriptase (Life Sciences, Inc.).

The reaction of reverse transcription of the messenger RNA to the complementary DNA (cDNA) takes place for 1 hour at 42° C.

The extent of synthesis of cDNA is calculated by measuring the level of incorporation of the radioactive tracer into acid-precipitable molecules, according to a known technique.

After 1 hour, the reaction is stopped by adding EDTA (20 mM), and the messenger RNA is destroyed by alkaline digestion in 50 mM NaOH at 42° C. for 3 hours.

The newly formed cDNA is separated from the nonincorporated dNTPs and the alkaline degradation products of the RNAs by chromatography, for example, on a column of Sephadex G100 (Pharmacia Fine Chemicals). 1.5 μg of single-stranded cDNA is obtained from 5 μg of total messenger RNA.

b. Synthesis of the second strand

The single-stranded cDNA is converted to double-stranded DNA by the action of the "Klenow" fragment of DNA polymerase I.

The reaction conditions are: 100 mM Hepes pH 7, 10 mM $MgCl_2$, 2.5 mM DTT, 70 mM KCl, 0.5 mM with respect to each dNTP and 50 units of DNA polymerase I "Klenow" fragment (marketed, for example, by New England Biolabs Inc.).

The reaction is carried out for 15 hours at 15° C., and the double-stranded DNA is separated from the nonincorporated dNTPs again by chromatography on a column of Sephadex G100.

c. Cloning of the double-stranded DNA

To eliminate the single-stranded DNA molecules and obtain a blunt-ended double-stranded DNA, the unpaired sequences are treated with $S_1$ nuclease according to the technique described by A. Efstradiatis et al., Cell (1976), 7, p. 279 et seq. The double-stranded newly formed DNAs are separated according to their size by centrifugation in a sucrose gradient. In general, a gradient of 5%–20% of sucrose in 50 mM Tris.HCl pH 8.5, 10 mM EDTA, 800 mM NaCl is used, centrifuged at 210,000 g for 15 hours at 20° C., and the gradient is fractionated into aliquots after centrifugation.

The size of the molecules in each fraction is monitored by electrophoresis of samples carried out in parallel with DNA standards of known sizes, and the fractions containing a DNA consisting of a chain of more than 500 base pairs are combined.

For the purpose of cloning this DNA, its 3' ends are first elongated with oligo(dC) and, in parallel, the 3' ends of the PstI site of the plasmid vector pBR322 are elongated with oligo(dG) according to the technique of F. Rougeon et al., J. Biol. Chem. (1977), 252, p. 2209 et seq.

The double-stranded DNA described above is then hybridized with the plasmid vector, for example according to the technique of L. Villa-Komaroff et al., Proc. Natl. Acad. Sci. (USA) (1978), 75, p. 3727 et seq.

A "library" of liver cDNA clones is created by transformation of *E. coli* bacteria with this hybridized DNA, according to the method described by M. Mandel and A. Higa, J. Mol. Biol. (1970), 53, p: 154 et seq., and M. Dagert and S. D. Erlich, Gene (1979), 6, p. 23 et seq.

d. Identification of the albumin cDNA clones

A colony hybridization technique is employed, using synthetic oligonucleotides the sequences of which are deduced from the protein sequence of human albumin [B. Meloun et al., FEBS Letters (1975), 58, p. 134 et seq.; M. Grunstein and D. Hogness, Proc. Natl. Acad. Sci. (USA) (1975), 72, p. 3961 et seq.; R. B. Wallace et al., Nucleic Acids Res. (1981), 9, p. 879 et seq.].

The clones are cultured in square dishes directly on nitrocellulose filters in series of 96 in Luria medium containing 25 μg/ml of tetracycline. After growth at 37° C. followed by amplification in the presence of 250 μg/ml of chloramphenicol, the colonies are lysed with sodium hydroxide and then hybridized with oligonucleotides which have been radioactively labelled at position 5' by kinase treatment, in a solution containing: 5×SSC, 0.5% NP 40, 100 μg/ml of salmon sperm DNA denatured by boiling and cooled rapidly in ice, and 0.5 ng/ml of kinase-treated oligonucleotide. The hybridization is performed at 37° C. for 18 hours. The filters are then washed in 5×SSC at 25° C., then at 37°

C. and then at 45° C., this being done four times for 15 minutes at each stage.

The filters are then exposed at −70° C. to Kodak X-OMAT film with an enhancing screen for 15 to 24 hours. The clones which hybridize with the probes are re-isolated and then lysed. The plasma DNA is purified by centrifugation in caesium chloride/ethidium bromide medium according to a known technique.

The DNA of the insertion is sequenced by the Maxam-Gilbert technique [A. Maxam and W. Gilbert, Methods Enzymol. (1980), 65, p. 499 et seq.] to compare the protein sequence derived from the nucleotide sequence with that of human serum albumin.

In this manner a series of clones is identified in which the insertions correspond to the whole human serum albumin gene.

FIG. 1 shows the restriction map of the serum albumin gene, as well as the position of three of the most representative insertions, designated "pT1B11", "pAA38" and "p6D8".

e. Incorporation of an initiation codon into the structural gene (FIG. 2)

(a) The DNA of plasmid "pT1B11" is digested with the enzymes PstI and PvuII, and a 125 base-pair DNA fragment is isolated corresponding to the sequence of the 5' end of the serum albumin gene (amino acids Nos. 1 to 62). At the PvuII end, a junction sequence is attached consisting of the site for recognition of the enzyme BamHI. A PstI-BamHI fragment is thereby obtained.

A synthetic oligonucleotide 21 bases long is prepared separately, the oligonucleotide possessing an "ATG" triplet in front of the nucleotides which code for the amino acids of human serum albumin and also an NcoI restriction site, and its sequence being as follows: 5'GAATCCATGGATGCACACAAG 3'.

The PstI-BamHI DNA fragment is denatured and hybridized with the synthetic oligonucleotide. The hybridization is accomplished through the sequence 5' ... GATGCACACAAG 3', the 3' end of the complementary DNA strand being unpaired. The unpaired ends are digested and polymerization is then carried out in the 5' ... 3' direction with DNA polymerase I Klenow fragment, according to the techniques of H. Jacobsen et al., Eur. J. Biochem. (1974), 45, p. 623 et seq.

A fragment is thereby obtained containing an NcoI site followed by the ATG triplet at the 5' end and a BamHI site at the 3' end.

(b) The ligation is carried out of three DNA fragments:

(1) an EcoRI-BamHI fragment of plasmid "pLG200" [L. Guarente et al., Cell (1980) 20p. 543 et seq.] carrying a gene for resistance to antibiotics, the origin of replication and the 3' end of the β-galactosidase gene, (2) an EcoRI-PvuII fragment of plasmid "pGL101" [G. Lauer et al., J. Mol. Appl. Genet. (1981), 1, p. 139 et seq.] carrying the P$_{lac}$ promoter and the ribosome binding site (RBS) of the E. coli LacZ gene, (3) the mutagenized DNA fragment described above which codes for the first 62 amino acids of human albumin.

A plasmid (pXL52) is isolated in which fusion of the 5' end of the human serum albumin gene with the E. coli β-galactosidase gene has been accomplished.

f. Construction of the complete gene (FIG. 2)

The DNA of plasmid "p6D8" is digested with EcoRI, and partially with BglII, according to a technique already described. The large EcoRI-BglII fragment, containing the sequence which codes for the last 405 amino acids of human serum albumin followed by the origin of replication of the plasmid and the gene for resistance to tetracycline, is isolated.

The DNA of plasmid "pXL52" described above is digested with EcoRI and Sau3A, and a fragment containing 200 base pairs is isolated.

The DNA of plasmid "pAA38" is digested with Sau3A and a fragment containing 540 base pairs is isolated.

The three fragments are ligated (in the order [pXL52 EcoRI-Sau3A]—[pAA38 Sau3A]—[p6D8 BglII-EcoRI]), turning to advantage the compatibility between the Sau3A and BglII sites. A plasmid known as "pXL53" is obtained, the quality of the construction of which is monitored by complete sequencing of the fragment between the EcoRI site and the PstI site corresponding to the junction between the insertion and the plasmid vector.

Figure 3F:

The complete nucleotide sequence, together with the derived protein sequence, are shown in FIGS. 3 and 4.

The observed variations between this sequence and the published protein sequence [B. Meloun et al., FEBS Letters (1975), 58, p. 134 et seq.; M. Dayhoff, Atlas of Protein sequence and structure (1978), 5, supplement 3, p. 306] are as follows:

| Position | Meloun et al. | Human serum albumin deduced from the sequence of "pXL53" |
| --- | --- | --- |
| 131 | Glutamine | Glutamic acid |
| 364 | Histidine | Alanine |
| 367 | Tyrosine | Histidine |
| 370 | Alanine | Tyrosine |
| 381 | Valine | Methionine |
| 464 | Glutamic acid | Histidine |
| 465 | Histidine | Glutamic acid |
| 501 | Glutamine | Glutamic acid |

B. CONSTRUCTION OF SYSTEMS FOR THE EXPRESSION OF HUMAN SERUM ALBUMIN

1. Use of bacteriophage lambda "P$_L$" promoter (a) Plasmid "pXL53" is linearized by partial digestion with the enzyme NcoI, with respect only to the NcoI site at the 5' end of the initiation codon, and blunt ends are formed by filling-in according to the technique of R. M. Wartell and W. S. Reznikoff, Gene (1980), 9, p. 307 et seq.

An "adaptor" is synthesized containing at the 5' end a sequence corresponding to the recognition site for a restriction enzyme such as BamHI, followed by a sequence corresponding to a ribosome binding site ("consensus" or "theoretical" RBS). The adaptor sequence is 5'GGATCCTAGGAGGAAC 3'.

The ligation of the adaptor at the 5' end of a blunt-ended DNA has been described, for example, by C. P. Bahl et al., Gene (1976), 1, p. 81 et seq.

The method consists in performing the reaction on 20 microliters of a solution containing 50 mM Tris.HCl pH 7.5, 10 mM MgCl$_2$, 15 mM DTT, 1 mM ATP, 50 μg/ml of adaptor, 20 μg/ml of DNA and 1 unit of DNA ligase (New England Biolabs Inc.). The reaction is carried out for 10 hours at 15° C. This ligation creates a BamHI site without eliminating the NcoI site.

The ligation product is digested with BamHI and with HinDIII. As a result of the presence of a HinDIII site at the 3' end of the human serum albumin gene, a DNA fragment containing the entire coding sequence is obtained.

The HinDIII-BamHI fragment thereby obtained is subcloned, for example, in plasmid "pBR322" by transforming E. coli according to the method described above to obtain plasmid "pXL61".

Plasmid "pXL61" does not contain any promoter.

Bacteriophage lambda "$P_L$" promoter is situated on the bacteriophage chromosome between a BglII site and a BamHI site [see E. Szybalski and W. Szybalski, Gene (1979), 7, p. 217 et seq.], and its nucleotide sequence is known [F. Sanger et al., J. Mol. Biol. (1982), 162, p. 279 et seq.]. This fragment can be cloned and its restriction sites modified according to known methods.

It is noted that plasmids carrying $P_L$ have to be propagated in E. coli strains carrying the repressor gene cI, in order to prevent this promoter from being expressed constitutively.

In a first construction, $P_L$ is available in the form of a BamHI fragment from plasmid "pP$_L$-lambda" (Pharmacia P. L. Biochemicals). By insertion of this BamHI fragment into the BamHI site of plasmid "pXL61", plasmid "pXL65" may be obtained, in which plasmid it has been verified that the orientation of promoter with respect to the structural gene for human serum albumin is correct.

Other constructions can be carried out from available plasmids. For example, it is possible to excise from plasmid "pP$_L$-lambda" an HaeIII-HaeIII fragment containing the $P_L$ promoter and insert it into the SmaI site of a multi-site cloning sequence carried by a plasmid, such as plasmid "pUC8" [J. Vieira and J. Messing, Gene (1982), 79, p. 259 et seq.], to obtain "pUC8-$P_L$" in which the EcoRI site is on the 5' side of the promoter.

Starting with plasmid "pPS1" [P. Sarmientos et al., Cell (1983), 32, p. 1337 et seq.], the HinDIII site closest to the NdeI site (FIG. 2) can first be destroyed and the small EcoRI-HinDIII fragment then replaced by, on the one hand the EcoRI-BamHI fragment of plasmid "pUC8-$P_L$" containing the $P_L$ promoter, and on the other hand the BamHI-HinDIII fragment of plasmid "pXL61" containing the serum albumin gene. Plasmid "pXL70" is thereby obtained, in which the assembly [$P_L$-"consensus" RBS-ATG-human serum albumin gene] is carried on an EcoRI-HinDIII DNA fragment.

(b) Replacement of the "consensus" RBS by that of the CII gene of bacteriophage lambda The CII gene of bacteriophage lambda, the sequence and the initiation site of which are known, can be efficiently translated [E. Schwarz et al., Nature (1978), 272, p. 410 et seq.].

A plasmid is constructed containing the expression system ["$P_L$" promoter-CII RBS-ATG-serum albumin gene].

For example, after the BamHI site of "pUC8-$P_L$" has been destroyed by the action of SI enzyme [A. J. Berck and P. A. Sharp, Cell (1977), 12, p. 721] an EcoRI-HinDIII fragment can be isolated containing the $P_L$ promoter, and the fragment can then be linked with an EcoRI-HinDIII fragment of plasmid "pDS20" [G. Duester et al., Cell (1982), 30, p. 855 et seq.] to obtain plasmid "pXL73".

The CII gene RBS is extracted from plasmid "pPS1". This plasmid is digested with NdeI and a BamHI adaptor is inserted after the formation of blunt ends. The RBS is then excised in the form of a HinDIII-BamHI fragment.

A plasmid "pXL88" in which this HinDIII-BamHI fragment is linked with the large HinDIII-BamHI fragment of plasmid "pXL73" is constructed first. In the new plasmid "pXL88", the CII RBS is inserted in the correct orientation with respect to the $P_L$ promoter, and the whole combination is present in a multi-site system in such a way that the $P_L$-CIII RBS assembly is carried on a 578 base-pair EcoRI-BamHI DNA fragment.

The 578 base-pair EcoRI-BamHI fragment is sub-cloned between the EcoRI and BamHI sites of plasmid "pMC1403" [M. J. Casadaban et al., J. Bacteriol. (1980), 143, p. 971 et seq.] which carries the β-galactosidase gene (lacZ) after the BamHi site. This construction leads to plasmid "pXL91" in which the β-galactosidase gene is expressed under the control of the [$P_L$-CII RBS] system.

The BamHI-BglII fragment of plasmid "pXL61" described above is sub-cloned in the BamHI site of plasmid "pMC1403". (The ligation of a BglII site in a BamHI site is possible, but excision by BamHI at BglII is no longer possible; there consequently remains only one BamHI site).

This construction ("pXL71") leads to the insertion of a 700 base-pair DNA fragment containing the sequence [BamHI-"consensus" RBS-ATG-NcoI-partial gene for serum albumin (coding for amino acids 1 to 218)-β-galactosidase gene].

This plasmid is cut with BamHI and SacI (the SacI site is present in the β-galactosidase gene) and inserted in plasmid "pXL91" described above in place of the preexisting BamHI-SacI fragment.

This then leads to plasmid "pXL97" in which the insertion has the following structure:

[EcoRI site-$P_L$-CII RBS-BamHI site-"consensus" RBS-NcoI site-ATG-partial gene for serum albumin-β-galactosidase gene].

Plasmid "pXL97" is digested with BamHI, and partially with NcoI with respect only to the NcoI site near to the initiation codon, and blunt ends are formed by the action of $S_1$ nuclease, and the plasmid is then closed up again. This manipulation on the one hand eliminates the "consensus" RBS DNA sequence, and on the other hand brings an ATG of the CII RBS into phase with the serum albumin sequence.

Plasmid "pXL136" is thereby obtained, which contains the sequence [EcoRI site-$P_L$-CII RBS-ATG-partial gene for serum albumin-β-galactosidase gene].

Since the partial gene for serum albumin possesses a PvuII site, plasmid "pXL136" is digested with EcoRI and PvuII, and a 760 base-pair fragment is extracted and inserted between the EcoRI and PvuII sites of plasmid "pXL70" described above. Plasmid "pXL139" is thereby obtained, which carries the structure [$P_L$-CII RBS-complete serum albumin gene] on an EcoRI-HinDIII fragment, like plasmid "pXL70", and which carries the substitution of the "consensus" RBS by that of the CII gene.

(c) Expression of serum albumin after induction of the "$P_L$" promoter

Inoculation is carried out of an isolated E. coli colony carrying the temperature-sensitive repressor gene of the "$P_L$" promoter (cI$^{ts}$ gene) and transformed by one of the plasmids "pXL65", "pXL70" and "pXL139".

When the bacterium is in exponential phase, the "$P_L$" promoter of the plasmid is induced by raising the incubation temperature very rapidly to 42° C. Incubation is continued for 90 minutes. A sample of the culture is withdrawn and the bacteria are lysed in a suspension containing 60 mM Tris.HCl pH 6.8, 2% SDS, 100 mM β-mercaptoethanol, 10% of glycerol and 0.1% of bromophenol blue for 5 minutes.

The proteins are separated by polyacrylamide gel electrophoresis according to the method of U. K. Laemli, Nature (1970), 227, p. 680 et seq. or that of K. Weber and M. Osborne, J. Biol. Chem. (1969), 244, p. 4406 et seq.

The proteins are transferred to a nitrocellulose filter [M. Bittner et al., Anal. Biochem. (1980) 102, p. 459 et seq.; E. J. Stellwsag and A. E. Dahlberg, Nucleic Acid Res. (1980), 8, p. 229 et seq.). The presence of human albumin is detected by immunology, either with antibodies to human albumin followed by binding of labelled protein A, or with biotin-labelled anti-albumin antibodies visualized by means of avidin-peroxydase complexes.

In this manner, the presence is demonstrated of a protein which reacts with antibodies to human albumin, which co-migrates with authentic albumin and which is only present in lysates of E. coli after induction of this bacterium at 42° C. in the presence of plasmid "pXL65", "pXL70" or "pXL139".

The level of human serum albumin produced under these conditions can be determined. The proportion of albumin reproducibly produced is of the order of 0.1% of the total proteins demonstrated in an E. coli lysate under denaturing conditions.

2. Use of the promoter of the trytophan operon ($P_{trp}$) in tandem with the penicillin amidase promoter of E. coli The introduction of the structural gene for human serum albumin behind an inducible bacterial promoter enables this protein to be expressed in E. coli. The levels of expression of the different systems described above are close to each other, and of the order of 1000 molecules of serum albumin per cell. These results are close to those obtained with similar systems such as those described in European Patent Applications EP 73,646 and EP 91,527. In particular, in European Patent Application EP 91,527, a maximum yield of 8,000 molecules per cell of a "polypeptide resembling human serum albumin" is noted. The protein obtained is not strictly identical to human serum albumin, and the levels produced are incompatible with the demands of industrial productivity. Moreover, the production of serum albumin is accompanied by a lethal effect of the producing bacterium.

It has now been found, and this forms the subject of the present invention, that the production of human serum albumin can be considerably improved by using a plasmid containing, after the gene for the pre-peptide of E. coli penicillin amidase, the structural gene for human serum albumin, the expression of which is controlled by two regulator genes in tandem.

More especially, the invention provides a process for preparing human serum albumin by culturing a bacterium such as E. coli containing a plasmid comprising, after the gene for the pre-peptide (signal peptide) of E. coli penicillin amidase, the structural gene for human serum albumin, the expression of which is controlled by the penicillin amidase promoter in tandem with an inducible promoter such as the promoter of the tryptophan operon "$P_{trp}$".

The promoter of the tryptophan operon of E. coli enables the expression of a gene to be induced when the strain of E. coli is cultured in the absence of tryptophan or in the presence of an analogue such as 3-indolylacrylic acid [C. Yanofsky et al., Nucleic Acids Res. (1981), 9, p. 6647 et seq.]. Such a promoter is available in plasmids such as "pDR720" (Pharmacia PL Biochemicals) [also see D. Russel and G. Bennett, Gene (1982), 20, p. 231 et seq.].

E. coli penicillin G amidase (PAM) (EC 3.5.11; penicillin aminohydrolase), which converts penicillin G to 6-aminopenicillanic acid, is produced by strains of E. coli such as E. coli ATCC 11105 [C. Kutzbach and E. Rauenbusch, Hoppe-Seyler's Z. Physiol. Chem. (1974), 354p. 45 et seq.; E. J. Vandamme, Economic Microbiology (1980), 5, p. 467 et. seq.]. This enzyme possesses a signal peptide which is normally excised by E. coli. The gene has been cloned and its primary structure defined by sequencing [H. Mayer et al., in "Plasmids of Medical, Environmental and Commercial Importance" (1979), K. N. Timmis and A. Pühler, editors, Elsevier/North-Holland Biomedical Press, p. 459 et seq. and W. Bruns et al., in "Third European Congress of Biotechnology", (1984) vol. III, Verlag Chemie, p. 371 et seq.]. The sequence of the signal peptide consists of an "ATG" translation initiation codon followed by 75 nucleotides which code for the 25 amino acids of the signal peptide. The gene for human serum albumin is fused to it in such a way that the translation phase is conserved. Thus, after translation, the first amino acid of the albumin (aspartic acid) is present at the junction of the site of excision of the signal peptide.

This construction can be carried out in the following manner:

A EcoRI-PstI fragment of the E. coli ATCC 11105 chromosome containing the PAM gene is inserted between the EcoRI and PstI sites of plasmid pBR 322. Plasmid "pXL20" is thereby obtained.

The HinDIII-HinDIII fragment of plasmid "pXL20" containing the PAM gene is then inserted in the same orientation as the $P_L$ promoter in the HinDIII site of plasmid "pXL73". Plasmid "pXL125" is thereby obtained, containing the sequence [$P_L$ promoter-PAM gene]. Plasmid "pXL125" is digested with NruI (blunt-ended site) and a BamHI synthetic restriction site is inserted into the site situated at the beginning of the PAM gene at 170 nucleotides from the HinDIII site. The BamHI-BamHI [NruI] fragment containing $P_L$ gives plasmid "pXL134" by ligation with itself.

The EcoRI-BamHI fragment of plasmid "pXL70" is then replaced by the EcoRI-BamHI fragment of plasmid "pXL134" containing the $P_L$ promoter, the PAM RBS and the beginning of the PAM gene. Plasmid "pXL137" is thereby obtained, containing the following sequence: EcoRI-$P_L$-PAM[promoter-RBS-nucleotides coding for the signal peptide]-BamHI-"consensus" RBS-ATG-serum albumin gene.

The EcoRI-SalI fragment of plasmid "pXL137" is replaced by that of plasmid "pDR720". Plasmid "pXL194" is obtained, which contains the following construction: EcoRI-$P_{trp}$-SalI-PAM[promoter-RBS-signal peptide nucleotides]-BamHI-"consensus" RBS-ATG-serum albumin gene.

The signal peptide/serum albumin fusion is carried out by in vitro mutagenesis after sub-cloning in bacteriophage M13mp10 [J. Messing, Methods Enzymol. (1984), 101, p. 20 et seq.] according to known techniques [J. P. Adelmar et al., DNA (1983), 2, p. 183). The quality of the fusion is verified by sequencing and the fused fragment is reinserted into plasmid "pXL194". Plasmid "pXL288" is thereby obtained, which possesses the following structure: EcoRI-$P_{trp}$-SalI-PAM[promoter-RBS-ATG-signal peptide nucleotides]-serum albumin gene.

E. coli strains such as E. coli E 103S or E. coli B are transformed with plasmid "pXL288".

A 16-hour culture of E. coli (pXL288) in rich medium is cultured at a dilution of 1/100 in enriched M9 minimal medium (0.1% casamino acids) without tryptophan, incubating at 37° C. with constant agitation. Growth is stopped at the end of the exponential phase and the bacteria are lysed ultrasonically and then centrifuged. The proteins in the supernatant and the pellet are analysed by electrophoresis under denaturing conditions. The level of human serum albumin obtained is of the order of 10% of the proteins observed under denaturing conditions.

Under these conditions, the production of human serum albumin is in the region of 10 mg per liter of medium, for an absorbence of 1 at 610 nm. Under these conditions, no lethal effect is observed on the bacterial strain.

In addition, conditions can be found such that the PAM/human serum albumin fusion, not matured in vivo, is digested with a peptidase specific for the "leader" sequences of E. coli [P. B. Wolf et al., J. Biol. Chem. (1982), 257, p. 7098 et seq.] to yield a protein identical to authentic human serum albumin.

We claim:

1. Process for the microbiological preparation of human serum albumin which comprises culturing an E. coli transformed with, and capable of maintaining a plasmid containing a DNA sequence encoding the signal peptide of E. coli penicillin amidase linked to the structural gene for human serum albumin, and having, operably linked to the penicillin amidase signal sequence human serum albumin gene and situated upstream thereof, the penicillin amidase promoter in tandem down stream of, with an inducible promoter, and isolating human serum albumin.

2. Process according to claim 6, in which the inducible promoter is that of the tryptophan operon, $P_{trp}$.

3. Process according to claim 6 in which the bacterium is E. coli transformed with a plasmid comprising the $P_{trp}$ promoter upstream of the E. coli penicillin amidase promoter, the ribosome binding site of the penicillin amidase gene, the ATG initiation codon and the nucleotides for the penicillin amidase signal peptide, fused with the structural gene for human serum albumin.

4. A plasmid containing the ribosome binding site of the penicillin amidase gene, the ATG initiation codon and the DNA sequence encoding the penicillin amidase signal peptide linked to the structural gene for human serum albumin, and having, operably linked to the human serum albumin gene and situated upstream thereof, the $P_{trp}$ promoter upstream of the E. coli penicillin amidase promoter."

* * * * *